United States Patent
Shi et al.

(10) Patent No.: US 11,324,665 B2
(45) Date of Patent: May 10, 2022

(54) MEDICATION INTELLIGENT DEVICE

(71) Applicant: National Applied Research Laboratories, Hsinchu (TW)

(72) Inventors: Shaw-Ben Shi, Hsinchu (TW); Shu-Hui Hung, Hsinchu (TW); Wei-Hua Teng, Hsinchu (TW)

(73) Assignee: National Applied Research Laboratories, Hsinchu (TW)

( * ) Notice: Subject to any disclaimer, the term of this patent is extended or adjusted under 35 U.S.C. 154(b) by 23 days.

(21) Appl. No.: 17/034,951

(22) Filed: Sep. 28, 2020

(65) Prior Publication Data

US 2021/0177702 A1 Jun. 17, 2021

(30) Foreign Application Priority Data

Dec. 13, 2019 (TW) .................. 108216561

(51) Int. Cl.
- G08B 21/00 (2006.01)
- A61J 7/00 (2006.01)
- A61J 7/04 (2006.01)
- G16H 20/13 (2018.01)

(52) U.S. Cl.
CPC .............. *A61J 7/0076* (2013.01); *A61J 7/04* (2013.01); *G16H 20/13* (2018.01); *A61J 2200/30* (2013.01)

(58) Field of Classification Search
CPC ........ A61J 7/0076; A61J 7/04; A61J 2200/30; A61J 1/03; A61J 2200/70; A61J 7/0418; A61J 7/0445; A61J 7/0481; G16H 20/13

USPC .......................................................... 340/5.7
See application file for complete search history.

(56) References Cited

U.S. PATENT DOCUMENTS

| | | | | |
|---|---|---|---|---|
| 4,869,392 | A * | 9/1989 | Moulding, Jr | A61J 7/0481 221/1 |
| 9,345,645 | B1 * | 5/2016 | Chernyak | A61J 7/049 |
| 2006/0071011 | A1 * | 4/2006 | Varvarelis | G07F 17/0092 221/9 |
| 2015/0360834 | A1 * | 12/2015 | Mikhail | G16H 20/13 340/384.5 |
| 2017/0281471 | A1 * | 10/2017 | Hamilton | A61J 7/0076 |
| 2019/0392936 | A1 * | 12/2019 | Arric | G16H 20/13 |

* cited by examiner

*Primary Examiner* — Mark S Rushing
(74) *Attorney, Agent, or Firm* — James W. Huffman; Huffman Law Group, PC

(57) ABSTRACT

A medical intelligent device is for use with a medical jar. The medical jar defines an accommodating space for containing at least one medicine. The medication intelligent device includes a cover and an auxiliary medicine deliver. The cover is detachably mounted on the medical jar. The auxiliary medicine deliver is disposed on the cover and includes a main control chip and a medicine delivery gate electrically connected to the main control chip. The main control chip is used to move the gate between a closed position and an opened position relative to the cover. In the closed position, the medicine delivery gate closes the accommodating space. In the opened position, the medicine delivery gate opens the accommodating space.

10 Claims, 4 Drawing Sheets

MEDICATION INTELLIGENT DEVICE

BACKGROUND OF THE INVENTION

1. Field of the Invention

The present invention is related to a medication device, and more particularly related to a medication intelligent device capable of increasing medicine compliance and providing monitoring service.

2. Description of Related Art

Correct medication behavior and medication habits can increase medication compliance and allow patients to achieve better treatment results. Conventional patent, such as Republic of China Patent No. 1645846, Republic of China Patent Publication No. 201737136, and U.S. Pat. No. 9,775,780, have disclosed and medical jar detect whether drugs have been removed or the remaining quantity of the pill boxes. The pill boxes can also provide the data related to the use of medicines so as to monitor and track the quantity of medicines taken by patients and remind patients to take medicines.

However, there are many reasons why patients do not follow the medication instructions. For example, the patients simply forgot to take the medicine or forgot the medicines have been taken and took the medicines twice. Or, the treatment plan is too complicated, and for example, there are too many types of medicines, the use time of each medicine is different, and the dosage is different, which causes difficulties for patients to use medicine. For certain diseases, such as high blood pressure, diabetes, hepatitis B, hepatitis C, cancer, AIDS, mental disorders, depression, etc., the use time and dosage of the drugs need to be especially cautious. It will bring a very high risk to the patients. Although the pill boxes described in the existing patent documents have the effect of monitoring and tracking the amount of medication taken by patients and reminding patients to take medication, those patents lack a mechanism that medical jar actually control the time and amount of medication used.

SUMMARY OF THE INVENTION

An objective of the present invention is to provide a medication intelligent device.

According to the aforementioned objective, a medication intelligent device communicably connected to a server and suitable to use with a medical jar, which defines an accommodating space for at least one medicine, and includes a cover and an auxiliary medicine delivery device. The cover detachably mounts the medical jar. The auxiliary medicine delivery device is disposed in the cover and includes a main control chip and a medicine delivery gate electrically connected to the main control chip. The main control chip is used to move the medicine delivery gate between a sealed position and an opened position relative to the cover, and the medicine delivery gate seals the accommodating space in the sealed position, and the medicine delivery gate opens the accommodating space in the opened position.

The cover includes a first cover portion and a second cover portion. The first cover portion is detachably disposed in the medical jar and the second cover portion is detachably connected to the first cover portion.

The medicine delivery gate is disposed in the first cover portion and an inner peripheral surface of the first cover portion defines a first through-hole, when the medicine delivery gate is in the sealed position, the medicine delivery gate blocks the at least one medicine located within the accommodating space from passing through the first through-hole; when the medicine delivery gate is in the opened position, the medicine delivery gate allows the at least one medicine located within the accommodating space passing through the first through-hole.

The auxiliary medicine delivery device further includes a sensing unit electrically connected to the main control chip. The sensing unit of the auxiliary medicine delivery device is disposed in a light blocking sensing module located in the inner peripheral surface of the first cover portion, and the light block sensing module outputs a sensing signal to the main control chip and the main control chip counts to acquire a current medicine quantity according to the sensing signal when the at least one medicine each passes through the first through-hole.

The auxiliary medicine delivery device is communicatively connected to the server and used to receive a medication use policy from the server, and the main control chip of the auxiliary medicine delivery device controls the medicine delivery gate to move between the sealed position and the opened position relative to the cover according to the medicine use policy and the current medicine quantity.

The medication intelligent device further includes a restricting element disposed within the accommodating space and the restricting element includes a first restricting portion connected to the first cover portion, and a caliber of the first restricting portion allows single one of the at least one medicine passing. The first restricting portion is communicated with the first through-hole when the medicine delivery gate is in the opened position.

The restricting element further includes a second restricting portion connected to the first restricting portion, and the second restricting portion includes a small end connected to the first restricting portion and a large end being away from the small end, and the caliber of the large end is larger than the caliber of the small end.

The large end of the second restricting portion of the restricting element abuts an inner peripheral of the medical jar.

The first restricting portion includes a cylindrical shape, and the second restricting portion includes a frustoconical shape.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art medical jar easily understand the objects and advantages of the present invention by referring to the disclosure of the specification, the claims, and the accompanying drawings.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE PREFERRED EMBODIMENT

These and other aspects of the embodiments herein will be better appreciated and understood when considered in conjunction with the following description and the accompanying drawings.

Figure 1:
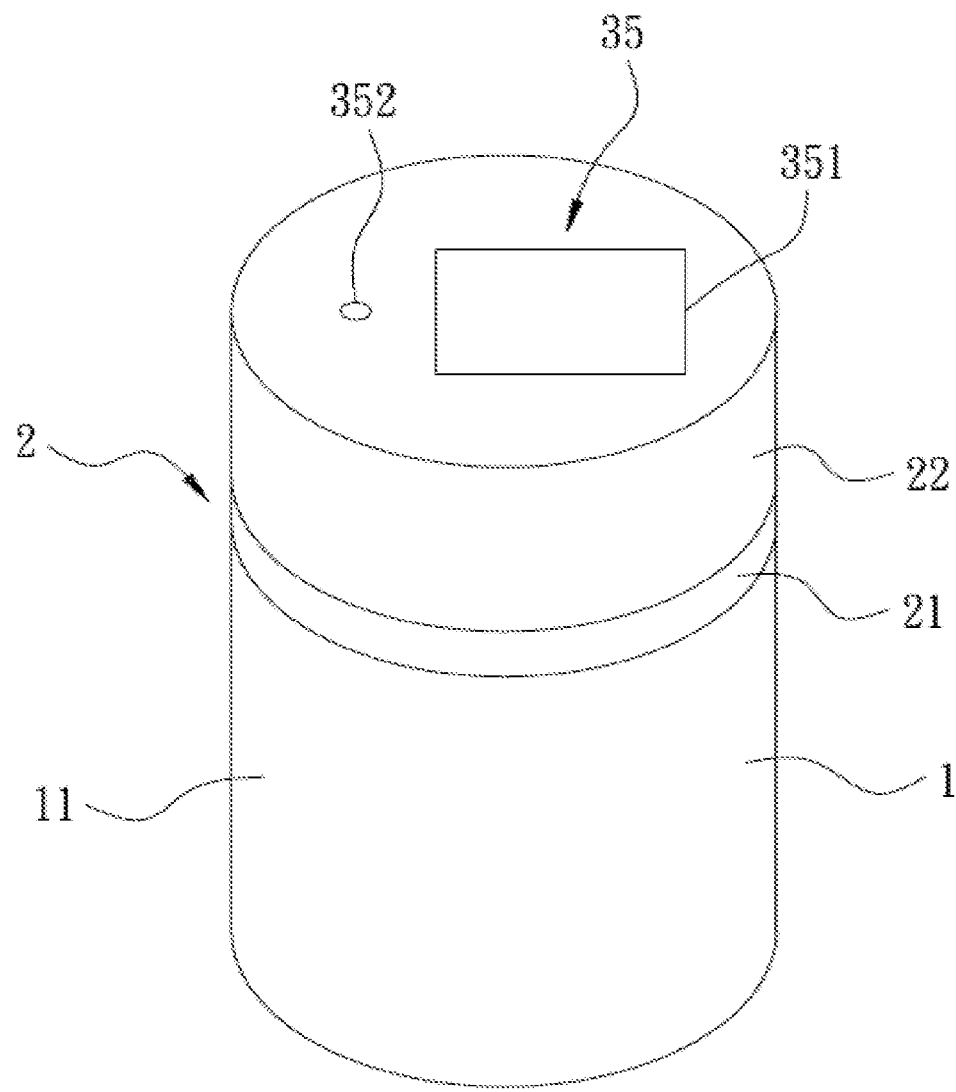
FIG. 1 is an outlook view illustrating a medication intelligent device in a preferred embodiment of the present invention.
Figure 2:
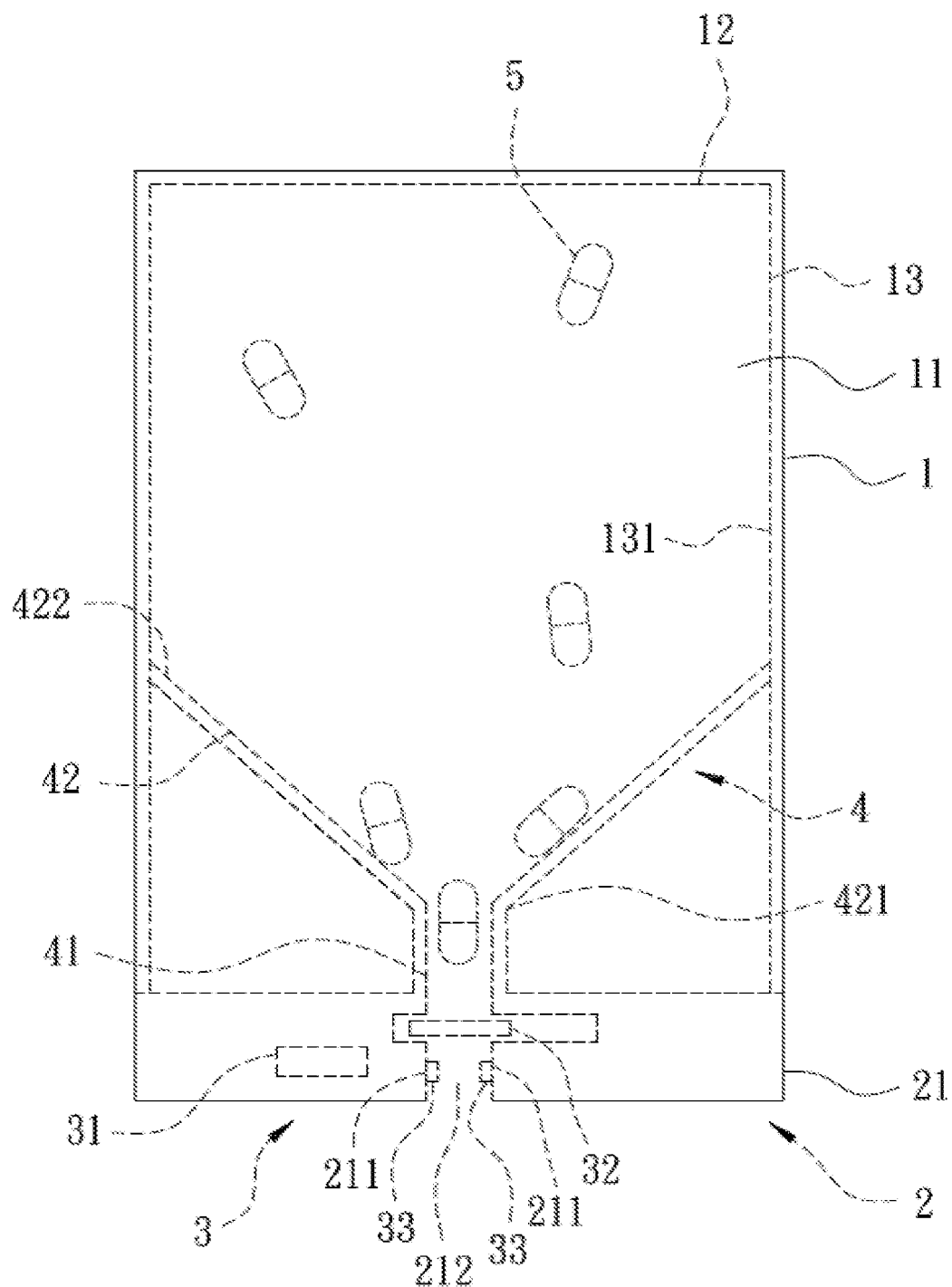
FIG. 2 is a schematic side view illustrating a medicine delivery gate of an auxiliary medicine delivery device of the medication intelligent device is in a sealed position.

Please refer to FIG. 1 and FIG. 2, the medication intelligent device in the preferred embodiment of the present invention is adapted for use with a medical jar 1 and the medical jar 1 includes an accommodating space 11. The medication intelligent device includes a cover 2, an auxiliary medicine delivery device 3 and a restricting element 4. The cover 2 is detachably covered on the medical jar 1 so as to seal the accommodating space 11. The auxiliary medicine delivery device 3 is installed in the cover 2, and the restricting element 4 is disposed in the accommodating space 11.

The medical jar 1 includes a first wall 12 and a surrounding wall 13 extending from the periphery of the first wall 12, and the first wall 12 and the surrounding wall 13 are jointly defined the accommodating space 11, which is used to accommodate at least one medicine 5. The cover 2 includes a first cover portion 21 detachably covered on the medical jar 1, and a second cover portion 22 detachably connected to the first cover portion 21. An inner peripheral surface 211 of the first cover portion 21 defines a first through-hole 212. The auxiliary medicine delivery device 3 is disposed on the first cover portion 21. The restricting element 4 includes a first restricting portion 41 connected to the first cover portion 21 of the cover 2 and a second restricting portion 42 connected to the first restricting portion 41. In the preferred embodiment, the first restricting portion 41 includes a cylindrical shape, and the caliber of the first restricting portion 41 can only allow a single medicine 5 to pass through, and the first restricting portion 41 and the first through-hole 212 have the same caliber. The second restricting portion 42 includes a frustoconical shape and has a small end 421 and a large end 422. The small end 421 is connected to the first restricting portion 41, and the large end 422 away from the first restricting portion 41 relative to the small end 421 and having a diameter larger than the small end 421. The large end 422 abuts an inner peripheral surface 131 of the surrounding wall 13 of the medical jar 1.

Figure 4:
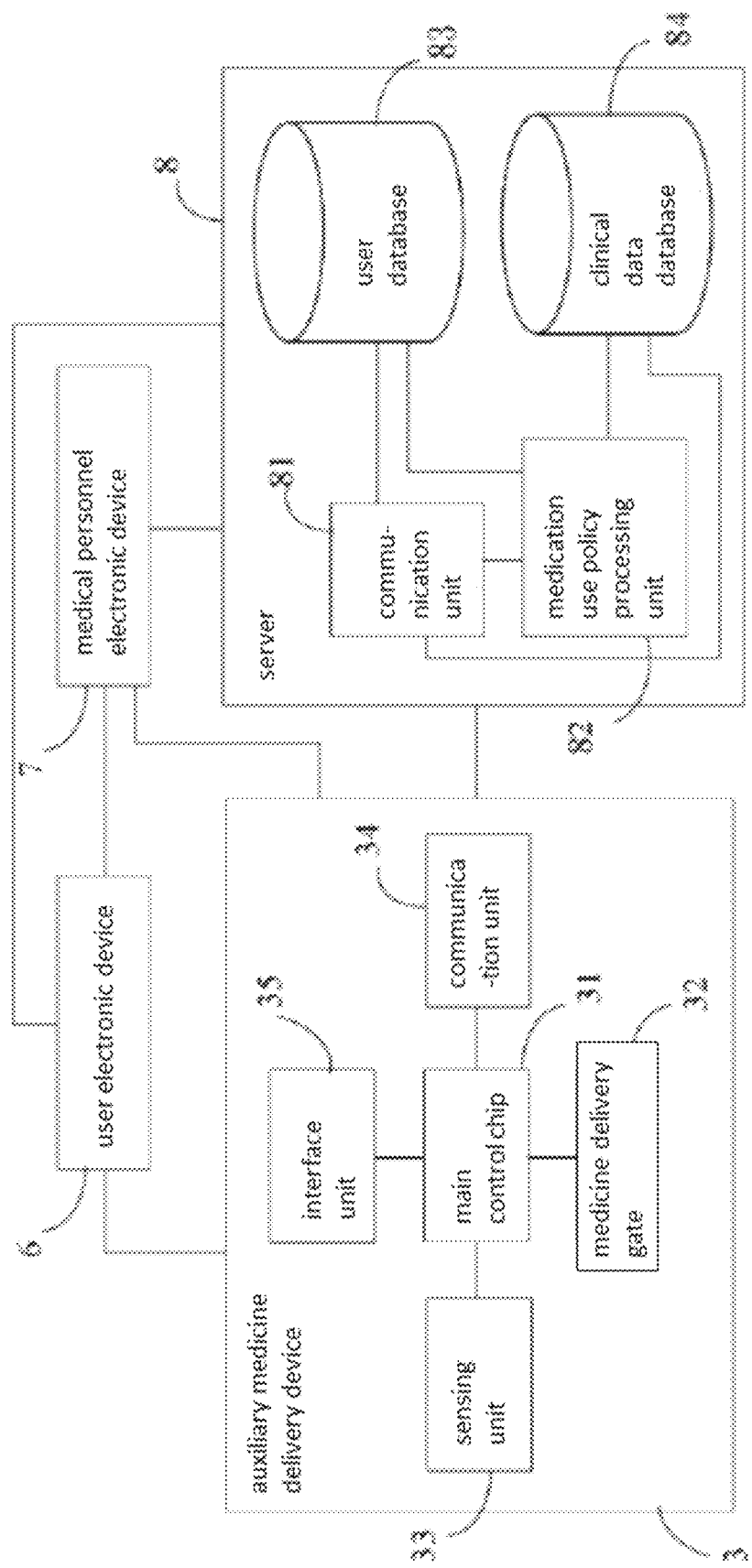
FIG. 4 is a functional block diagram illustrating an embodiment thin the medication intelligent device is used in a medication compliance and monitoring system in the present invention.

Please refer to FIG. 1, FIG. 2 and FIG. 4, and further, the auxiliary medicine delivery device 3 includes a main control chip 31, a medicine delivery gate 32, a sensing unit 33, a communication unit 34 and an interface unit. The medicine delivery gate 32, the sensing unit 33, the communication unit 34 and the interface unit are electrically connected to the main control chip 31, respectively. The interface unit 35 includes an operation screen 351 disposed on the second cover portion 22 and an indicator light 352.

Figure 3:
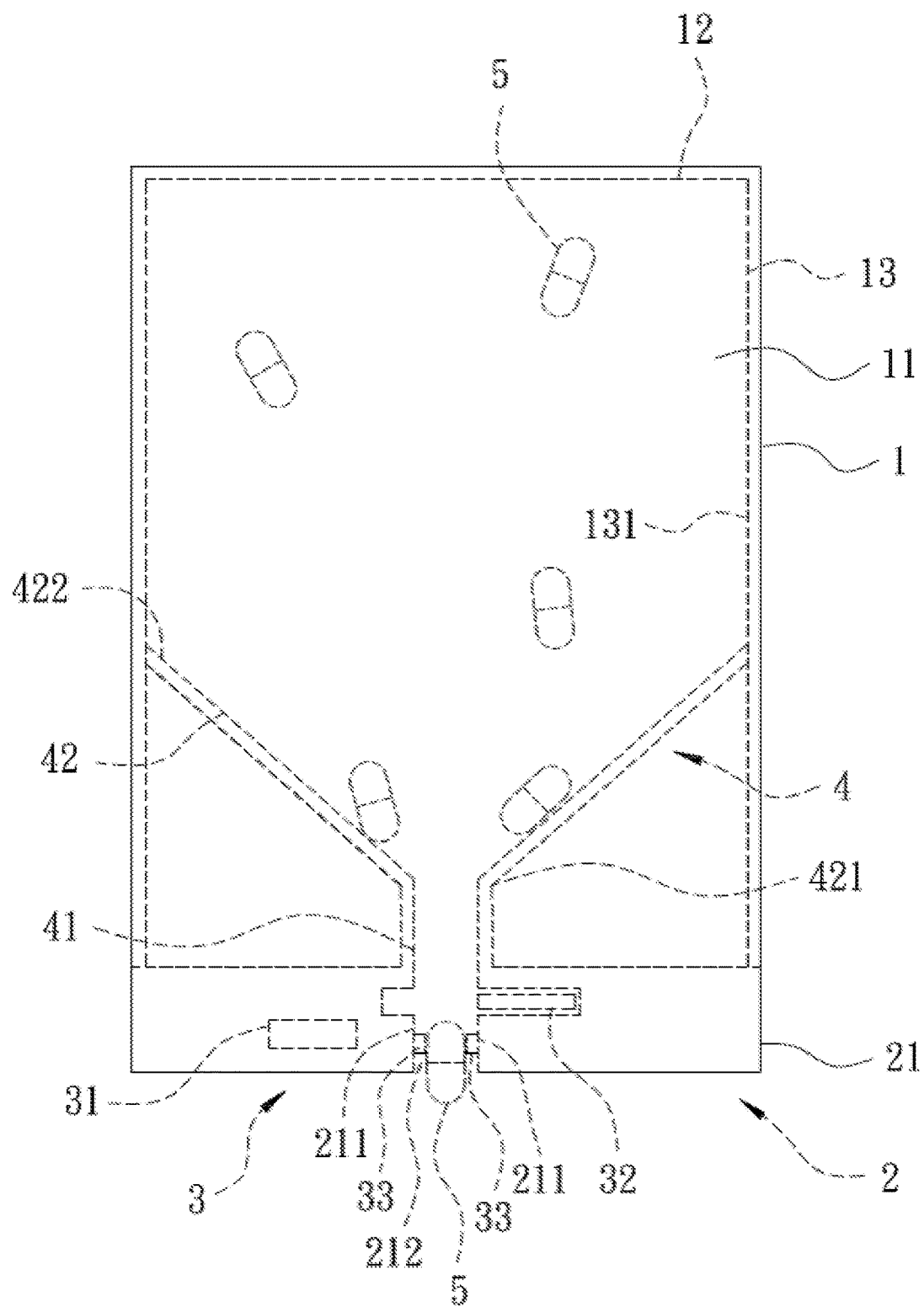
FIG. 3 is a schematic side view illustrating the medicine delivery gate of the auxiliary medicine delivery device of the medication intelligent device is in a opened position.

Please refer to FIG. 2, FIG. 3 and FIG. 4, the main control chip 31 is used to move the medicine delivery gate 32 between a sealed position and an opened position relative to the cover 2. As shown in FIG. 2, in the sealed position, the medicine delivery gate 32 seals the accommodating space 11 to block the medicine 5 located within the accommodating space 11 from passing through the first through-hole 212. As shown in FIG. 3, in the opened position, the medicine delivery gate 32 opens the accommodating space 11 to allow the medicine 5 located within the accommodating space 11 passing through the first through-hole 212. In the preferred embodiment, the sensing unit 33 is a light-blocking sensing module 33 disposed on the inner peripheral surface 211 of the first cover portion 21.

Please refer to FIG. 1, FIG. 3 and FIG. 4, when the user needs medicine, the second cover part 22 of the cover 2 is opened and the main control chip 31 moves the medicine delivery gate 32 to the opened position. At this time, the first restricting portion 41 is communicated with the first through-hole 212, and the medicine 5 sequentially passes through the first restricting portion 41 and the first through-hole 212 to the user. It should be noted thin the design of the restricting element 4 allows the medicine 5 to pass through the first restricting portion 41 and the first through-hole 212 in order of one piece at a time. When each medicine 5 passes through the first through-hole 212, the light-blocking sensing module 33 outputs a sensing signal to the main control chip 31 for accurate counting.

The following description cooperates with an example. The medication intelligent device is applied with a medication compliance assisting and monitoring system. The medication compliance assisting and monitoring system includes a user electronic device 6, a medical personnel electronic device 7 and a server 8. The auxiliary medicine delivery device 3 of the medication intelligent device, the user electronic device 6, the medical personnel electronic device 7 and the server 8 are connected communicatively to each other. The server 8 includes a communication unit 81, a medication use policy processing unit 82 electrically connected to the communication unit 81, a user database 83 electrically connected to the communication unit 81 and the medication use policy processing unit 82 and a clinical data database 84 electrically connected to the communication unit 81 and the medication use policy processing unit 82. Furthermore, the user database 83 and the clinical data database 84 are created in advance, and the user database 83 includes at least one medication information of the user (patient) and at least one questionnaire data. The clinical data database 84 includes clinical information and data related to different diseases. The medication use policy processing unit 82 has built-in determining rules and algorithms.

When the user firstly obtains the medication intelligent device, the user electronic device 6 (e.g., a handheld device) and the medication intelligent device are tested for connection pairing.

If the pairing is unsuccessful, a pairing failure message is sent to the medical personnel electronic device 7. In the present embodiment, the operator for the medical personnel electronic device 7 is a case manager who takes care of the user.

If the pairing is successful, the user downloads a medication assistance application to the user electronic device 6, and enters personal information of the user through the medication assistance application. Then, the user electronic device 6 transmits the user's personal data to the server 8. After the personal data is received by the communication unit 81 of the server 8, the user data is written by the use policy processing unit 82 in the user database 83. The use policy processing unit 82 also obtains a corresponding medicine use regulation (including at least one using time of the medicine of the user and the corresponding medication quantity at each time point) of the user according to the personal data, the medication information and the questionnaire data in the user database 83, and the clinical information and data in the clinical data database 84. The medicine use regulation is transmitted to the auxiliary drug dispenser 3, the user electronic device 6, and the medical personnel electronic device 7 through the communication unit 81.

Thereafter, according to the medicine use regulation received by the communication unit 34, the main control chip 31 of the auxiliary drug dispenser 3 displays a medication instruction on the operation screen 351 of the interface unit 35 cooperated with a reminding light 352 when the user needs medication. The main control chip 31 also moves the medicine delivery gate 32 to the opened position according to the medicine use regulation, and the medicine 5 sequentially passes through the first restricting portion 41 and the first through-hole 212 to the user's hand. When a medicine 5 passes through the first through-hole 212, the light-blocking sensing module 33 outputs the sensing signal to the main control chip 31 for counting. When the main control chip 31 counts the current medication quantity being equal to the medication quantity in the time point of the medicine use regulation, the master control chip 31 moves the medicine delivery gate 32 to the sealed position (as shown in FIG. 2) to block the medicine 5 located within the accommodating space 11 from passing through the first through-hole 212.

After each medication time, the main control chip 31 transmits the actual medication information of the user to the medical personnel electronic device 7 and the server 8 through the communication unit 34 for recording, tracking, and monitoring. In the present embodiment, the user's actual medication data includes the current medication quantity and actual medication time. The medication use policy processing unit 82 of the server 8 updates the user database 83 according to the actual medication information of the user received by the communication unit 81. It should be noted that when the user forgets to take the medicine at that time, the current quantity of medicines in the user actual medication data is 0.

The medication use policy processing unit 82 will further update the medicine use regulation of the user according to the actual medication data of each user and the information in the user database 83 and the clinical data database 84. In some circumstances, for example, the user often forgets to take the medicine. At this time, the server 8 further sends a warning message to the auxiliary medicine delivery device 3 of the medication intelligent device, the user electronic device 6 and the medical personnel electronic device 7. The main control chip 31 of the auxiliary applicator 3 further displays the warning message on the operation screen 351 of the interface unit 35. The user electronic device 6 will also display the warning message, and the case manager in the end of the medical personnel electronic device 7 can receive the warning message and further contacts by phone to understand the user status and remind to take the medicine.

At each period of time, the medication use policy processing unit 82 of the server 8 also sends a questionnaire to the user electronic device 6 through the communication unit 81. After the user completes the questionnaire using the user electronic device 6, the questionnaire will be sent back to the server 8 and the medication use policy processing unit 82 will update the user database 83 according to the questionnaire received by the communication unit 81.

Please refer to FIG. 2, FIG. 3 and FIG. 4, in summary, the efficacy of the medication intelligent device in the present invention includes:

Firstly, the main control chip 3 moves the medicine delivery gate 32 between the sealed position and the opened position according to the medicine use regulation provided by the server 8, and can actively controls the time and quantity of medication.

Secondly, through the design of the restricting element 4, the medicine 5 can pass through the first restricting portion 41 and the first through-hole 212 in order of once at a time. When each medicine 5 passes the first through-hole 212, the light-blocking sensing module 33 outputs the sensing signal to the main control chip 3 for accurate counting. Accordingly, the medication intelligent device can actually control the use time and dosage of the medicine 5, and can also provide the actual medication information of the user to the medical personnel electronic device 7 and the server 8 for recording, tracking and monitoring. Further, the server 8 is able to accordingly update the medication intelligent device. The medication intelligent device not only greatly improves the compliance of the user to take medication, but also improves the efficacy of medication. Therefore, the medication intelligent device can indeed achieve the purpose of the present invention.

While the present invention has been described in terms of what are presently considered to be the most practical and preferred embodiments, it is to be understood thin the present invention need not be restricted to the disclosed embodiment. On the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the present invention which is defined by the appended claims.

What is claimed is:

1. A medication intelligent device communicably connected to a server and suitable to use with a medical jar, which defines an accommodating space for at least one medicine, and comprising:
    a cover detachably mounting the medical jar; and
    an auxiliary medicine delivery device disposed in the cover and including:
        a first cover portion detachably disposed in the medical jar; wherein the first cover portion comprises:
            a main control chip and a medicine delivery gate electrically connected to the main control chip;
            wherein the main control chip is used to move the medicine delivery gate between a sealed position and an opened position relative to the cover; and
            the medicine delivery gate seals the accommodating space in the sealed position, and the medicine delivery gate opens the accommodating space in the opened position; and
        a second cover portion detachably connected to the first cover portion;
            wherein upon opening the second cover portion, the main control chip moves the medicine delivery gate to the opened position or sealed position.

2. The medication intelligent device of claim 1, wherein:
    the medicine delivery gate is disposed in the first cover portion and an inner peripheral surface of the first cover portion defines a first through-hole, when the medicine delivery gate is in the sealed position, the medicine delivery gate blocks the at least one medicine located within the accommodating space from passing through the first through-hole;

when the medicine delivery gate is in the opened position, the medicine delivery gate allows the at least one medicine located within the accommodating space passing through the first through-hole.

3. The medication intelligent device of claim 2, wherein the auxiliary medicine delivery device further includes a sensing unit electrically connected to the main control chip.

4. The medication intelligent device of claim 3, wherein the sensing unit of the auxiliary medicine delivery device is disposed in a light blocking sensing module located in the inner peripheral surface of the first cover portion, and the light block sensing module outputs a sensing signal to the main control chip and the main control chip counts to acquire a current medicine quantity according to the sensing signal when the at least one medicine each passes through the first through-hole.

5. The medication intelligent device of claim 4, wherein the auxiliary medicine delivery device is communicatively connected to the server and used to receive a medication use policy from the server, and the main control chip of the auxiliary medicine delivery device controls the medicine delivery gate to move between the sealed position and the opened position relative to the cover according to the medicine use policy and the current medicine quantity.

6. The medication intelligent device of claim 2, further comprising a restricting element disposed within the accommodating space and the restricting element includes a first restricting portion connected to the first cover portion, and a caliber of the first restricting portion allows single one of the at least one medicine passing.

7. The medication intelligent device of claim 6, wherein the first restricting portion is communicated with the first through-hole when the medicine delivery gate is in the opened position.

8. The medication intelligent device of claim 6, wherein the restricting element further includes a second restricting portion connected to the first restricting portion, and the second restricting portion includes a small end connected to the first restricting portion and a large end being away from the small end, and the caliber of the large end is larger than the caliber of the small end.

9. The medication intelligent device of claim 8, wherein the large end of the second restricting portion of the restricting element abuts an inner peripheral of the medical jar.

10. The medication intelligent device of claim 9, wherein the first restricting portion includes a cylindrical shape, and the second restricting portion includes a frustoconical shape.

* * * * *